United States Patent [19]
Holmes et al.

[11] 4,393,167
[45] Jul. 12, 1983

[54] POLYMER BLENDS CONTAINING POLYMER OF β-HYDROXYBUTYRIC ACID AND CHLORINE OR NITRILE GROUP CONTAINING POLYMER

[75] Inventors: Paul A. Holmes, Middlesbrough; Frank M. Willmouth, Royston; Alan B. Newton, Welwyn Garden City, all of England

[73] Assignee: Imperial Chemical Industries PLC, London, England

[21] Appl. No.: 320,127

[22] Filed: Nov. 10, 1981

[30] Foreign Application Priority Data

Nov. 18, 1980 [GB] United Kingdom ............... 8036967

[51] Int. Cl.³ .................. C08L 67/04; C08L 27/06; C08L 33/18
[52] U.S. Cl. .................................. 525/64; 525/186; 525/190; 525/412; 525/415; 525/450
[58] Field of Search ................ 525/64, 190, 186, 450, 525/412, 415; 528/361

[56] References Cited

U.S. PATENT DOCUMENTS

| 3,182,036 | 5/1965 | Baptist et al. | 524/208 |
| 3,379,794 | 4/1968 | King et al. | 525/186 |
| 3,557,252 | 1/1971 | Hsieh et al. | 525/415 |
| 3,592,877 | 7/1971 | Mullins | 525/186 |
| 3,904,579 | 9/1975 | Braddicks | 525/186 |

OTHER PUBLICATIONS

J. App. Polymer Science, vol. 22, (1978) pp. 1255–1265, Sundgren et al.
Macromoles, vol. 13, (1980), pp. 365–369, Aubin et al.
Chem. Abstracts 95:82211t, Hummel et al.

Primary Examiner—Wilbert J. Briggs, Sr.
Attorney, Agent, or Firm—Cushman, Darby & Cushman

[57] ABSTRACT

Polymer blends containing (i) 0.2–95% by weight of a high molecular weight β-hydroxybutyric acid homo- or copolymer and (ii) a polymer containing at least 25% by weight of chlorine or nitrile groups, such as chlorinated polyethylene, polyvinyl chloride, or a high acrylonitrile resin.

In small quantities the β-hydroxybutyric acid polymer acts as a processing aid for the chlorine or nitrile containing polymer.

In larger quantities the properties of the β-hydroxybutyric acid polymer or the chlorine or nitrile containing polymer are improved.

20 Claims, No Drawings

POLYMER BLENDS CONTAINING POLYMER OF β-HYDROXYBUTYRIC ACID AND CHLORINE OR NITRILE GROUP CONTAINING POLYMER

This invention relates to polymer blends and in particular to polymer blends containing a β-hydroxybutyric acid polymer.

Poly(β-hydroxybutyric acid) is a thermoplastic polyester consisting of repeat units of the formula $$-CH(CH_3).CH_2.CO.O-$$

which is accumulated by many micro-organisms, particularly bacteria, for example of the genera Alcaligenes, Athiorhodium, Azotobacter, Bacillus, Nocardia, Pseudomonas, Rhizobium, and Spirillium, as an energy reserve material.

The polymer is conveniently prepared by cultivating the micro-organism in an aqueous medium on a suitable substrate, such as a carbohydrate or methanol, as an energy and carbon source. The substrate must, of course, be one that is assimilable by the micro-organism. In order to promote accumulation of the polymer, at least part of the cultivation is preferably conducted under conditions wherein there is a limitation of a nutrient that is essential for growth of the micro-organism but which is not required for polymer accumulation. Examples of suitable processes are described in European Patent Specification No. 15669 and in European patent application No. 81.303373.

Polymers containing both β-hydroxybutyric acid units and other hydroxycarboxylic acid units, such as β-hydroxyvaleric acid units, can also be produced microbiologically. Thus a microbiologically produced heteropolymer containing β-hydroxybutyric acid and β-hydroxyvaleric acid residues is described by Wallen et al. in "Environmental Science and Technology" 8 (1974) 576–9. Also, as described in United Kingdom patent application No. 81.20991 various copolymers can be produced by cultivating the micro-organism on certain substrates, such as propionic acid which gives rise to β-hydroxyvaleric acid units in the copolymer.

While cells containing the polymer can be used as such as a moulding material, for example as described in U.S. Pat. No. 3,107,172, it is generally desirable to separate the polymer from the remainder of the cell material.

Methods that have been proposed to effect this separation include breakage of the cells by methods such as treatment with acetone, followed by extraction of the polymer from the broken cells by treatment with a solvent in which the polymer is soluble. Examples of such processes are described in U.S. Pat. Nos. 3,036,959 and 3,044,942 in which the solvents employed are pyridine or mixture of methylene chloride and ethanol. Other extraction solvents for the polymer in the form in which it is produced in the cells include cyclic carbonates such as 1,2-propylene carbonate (see U.S. Pat. No. 4,101,533); chloroform (see U.S. Pat. No. 3,275,610); and 1.2-dichloroethane (as disclosed in European Patent Specification No. 15123).

U.S. Pat. No. 3,275,610 discloses other methods of cell breakage viz. ultrasonic vibration, grinding, French pressing, freezing/thawing cycles and lysozyme treatment, while, as described in the aforementioned European Patent Specification No. 15123, spray or flash drying of the suspension of cells as produced by culturing the micro-organism can also cause sufficient cell breakage to enable the polymer to be extracted from the cells.

Copolymers can also be made containing units of other hydroxycarboxylic acids and/or units derived from diols, e.g. ethylene glycol, and/or dicarboxylic acids, e.g. isophthalic acid, by ester interchange occurring when the microbiologically produced polymer or copolymer is melted with such a hydroxycarboxylic acid, lactone thereof, e.g. pivalolactone, diol, dicarboxylic acid and/or polyester produced therefrom.

In the following description therefore by the term HB polymer we mean not only the homopolymer, poly(β-hydroxybutyric acid) but also copolymers as described above, provided that the β-hydroxybutyric acid residues form at least 50 mole %, and preferably at least 60, particularly at least 80, mole % of the polymer chain.

When polymeric materials are used to form shaped articles by fabrication processes such as solution casting or processes involving melt shaping, for example injection or compression moulding, or extrusion, it is often useful to incorporate additives into the polymer in order to modify its properties and/or to assist the processing operation. Such additives may in some cases be other polymers.

We have found that HB polymers are useful additives for incorporation into certain other polymers and, likewise, certain other polymers are useful as additives for HB polymers.

In order to give the optimum physical properties, the HB polymer should be of high molecular weight, above 50,000, as determined by intrinsic viscosity measurements in chloroform at 30° C. using the intrinsic viscosity—molecular weight relationship derived by Einaga et al. (Macromoles 9 (1976) page 774–780, viz $(\eta) = 1.18 \times 10^{-4} Mw^{0.78}$. By intrinsic viscosity we mean the value obtained by plotting values of the fraction:

$$(t - i_o)/t_o c$$

where t is the flow time of a "c" gms deciliter$^{-1}$ solution of the PHB in a given solvent through a given viscometer, and $t_o$ is the flow time of the same volume of pure solvent through the same viscometer under the same conditions, against the concentration c for various values of c, and extrapolating the curve obtained to zero concentration.

Synthetic HB polymers, e.g. as prepared by polymerising β-butyrolactone, in common with other synthetic lactone polymers such as polypropiolactone or polycaprolactone, generally have only low molecular weights, below 50,000, which adversely affects the physical properties of articles made from blends containing such synthetic polylactones. In contrast, microbiologically produced HB polymers generally have a high molecular weight, above 50,000, and often above 200,000. We have found that the best results are achieved using HB polymers of molecular weight above 100,000.

In general, in order to obtain a benefit in the processing or other properties, the base polymer and additive polymer should exhibit some compatability: for this reason the polymers, for which HB polymers are useful additives, or which are usefully incorporated into HB polymers, are those containing at least 25% by weight of chlorine and/or nitrile groups. The chlorine atoms or nitrile groups appear to render the polymer capable of interaction with HB polymers, possibly by enabling hydrogen bonding to occur with the carbonyl groups of the HB polymer, resulting in at least partial miscibility between the polymers.

In general, although not exclusively so, the chlorine or nitrile group containing polymer should be used at a concentration at which it is miscible with the HB polymer. In fact, it may be advantageous to exceed the bounds of miscibility and a proportion of immiscible material may have desirable effects.

A useful test of miscibility is derived from examination of the characteristics of the blends as examined using differential thermal calorimetry or dynamic mechanical analysis techniques. The observation of a single, compositional dependent, peak characteristic of the glass transition temperature (Tg) is evidence that the polymers of the blend are miscible. The presence of two distinct Tg's at the temperatures characteristic of the Tg's of the pure homopolymers indicates immiscibility between the phases.

Accordingly we provide a polymer blend comprising (i) 0.2 to 95% by weight of an HB polymer of molecular weight above 50,000 and containing at least 50 mole % of β-hydroxybutyric acid residues in the polymer chain, and (ii) an organic polymer containing at least 25% by weight of chlorine atoms and/or nitrile groups.

We have found that such blends exhibit interesting characteristics; the properties of the blend naturally depend upon the nature and amount of the polymer blended with the HB polymer.

Examples of polymers that may usefully be blended with HB polymers include (i) polymers containing at least 50% by weight of units derived from vinyl chloride, vinylidene chloride and/or acrylonitrile, and 0 to 50% by weight of units derived from at least one ethylenically unsaturated monomer. Examples of such comonomers include olefins such as ethylene, propylene, and styrene; vinyl acetate; vinyl ethers; and ethylenically unsaturated acids and alkyl esters thereof wherein the alkyl group contains up to 6 carbon atoms, such as acrylic, methacrylic, maleic, or itaconic acids, ethyl acrylate, methyl acrylate, butyl acrylate, and methyl methacrylate.

(ii) chlorinated or chlorosulphonated hydrocarbon polymers. Examples of such hydrocarbon polymers include polyolefins such as polyethylene, polypropylene, and ethylene/propylene copolymers; polyisoprene; and polybutadiene. Preferred chlorinated hydrocarbon polymers include chlorinated polyethylene and chlorosulphonated polyethylene. The hydrocarbon polymers may be chlorinated or chlorosulphonated, in solution (which gives homogeneous products) or in suspension (which tends to give more heterogeneous materials).

(iii) chlorine containing polyethers.

The polymer blend contains 0.2 to 95% by weight of the HB polymer, based on the combined weights of the HB polymer and the chlorine or nitrile group containing polymer.

Addition of minor amounts, i.e. up to 50% by weight, of the HB polymer to the chlorine or nitrile group containing polymer generally assists the processing of the latter. Benefits in processability may be achieved by the addition of relatively small amounts of the HB polymer, e.g. 0.2 to 10, particularly 0.5-5, % by weight, and so here the HB polymer acts as a high molecular weight processing aid.

Hence addition of HB polymers, even in such relatively small amounts, enables polymers containing a major proportion of acrylonitrile, vinyl chloride, or vinylidene chloride units, that are difficult to melt process, to be melt processed more readily. Such polymers often have to be melt processed at a temperature relatively close to their melting points and often this means that the melt viscosity is relatively high. The addition of a small amount of a HB polymer causes, inter alia, the melt viscosity to be reduced and assists processability in other respects. To be effective as a processing aid, the HB polymer should have a melting point below the processing temperature: therefore, where the desired processing temperature is very near to, or below, the melting point, circa 180° C., of β-hydroxybutyric acid homopolymer, a lower melting copolymer containing β-hydroxybutyric acid units and a minor proportion, e.g. 1 to 40, particularly 2 to 20, mole %, of comonomer units, e.g. β-hydroxyvaleric acid units, is preferably employed. Such copolymers are particularly useful as processing aids for vinyl chloride polymers.

To avoid thermal degradation of the HB polymer, the processing temperature should be below 220° C.

HB polymers, both β-hydroxybutyric acid homopolymer and copolymers containing β-hydroxybutyric acid residues and comonomer residues, are useful as processing aids for the so-called high acrylonitrile resins often used because of their good impermeability to water and gases. Such resins, which contain at least 50% by weight of acrylonitrile, often present processing difficulties. Examples of such high acrylonitrile resins are graft copolymers obtained by the polymerisation of (a) 99.5 to 50% by weight of a monomeric material containing (i) at least 50% by weight of acrylonitrile and (ii) 0 to 50% by weight of at least one comonomer, such as styrene or an alkyl acrylate or methacrylate, e.g. methyl acrylate, in the presence of (b) 0.5 to 50% by weight of a butadiene) acrylonitrile copolymer. The incorporation of HB polymers, particularly a homopolymer of β-hydroxybutyric acid, as a processing aid is very effective in improving the processability and yet the impermeability characteristics of the acrylonitrile resin are not unduly affected.

Articles made by melt processing compositions containing a major proportion of a HB polymer are often relatively highly crystalline, although where copolymers containing, for example β-hydroxyvaleric acid residues, are employed, the crystallinity may be somewhat reduced. This high crystallinity often renders brittle articles fabricated from the polymer. It is therefore often desired, when using HB polymers as moulding materials, to improve the toughness of the HB polymer by incorporation of an impact modifier.

Rubbery chlorine or nitrile group containing polymers, for example chlorinated or chlorosulphonated polyolefins, such as polyethylene or ethylene/propylene copolymers, or chlorinated polyethers can exhibit a toughening effect on HB polymers and so act as impact modifiers therefor. To be effective as an impact modifier, the additive polymer should have a glass transition temperature, Tg, below 10° C. Preferably the amount of impact modifier forms 10 to 50% by weight, based on the combined weight of the impact modifier and the HB polymer.

It is thought that the toughening effect results since, although the rubbery polymers may not be completely miscible, in the proportions employed, with the HB polymer, the chlorine atoms or nitrile groups enable hydrogen bonding between the HB polymer and the rubber to occur, hence promoting interaction between the phases.

Other impact modifiers commonly used, such as ethylene/vinyl acetate copolymers, and ABS resins, which contain less than 25% by weight of nitrile groups, appear not to be effective as impact modifiers for HB polymers.

The preferred impact modifiers are chlorinated polyolefins, particularly chlorinated polyethylene containing up to 50% by weight of chlorine. However materials containing up to 70% by weight, or more, of chlorine may be used provided the Tg is below 10° C. In general, there should be sufficient chlorine present to lower the crystallinity of the polymer with respect to the unchlorinated polyolefin, but insufficient to increase Tg to above 10° C. Other suitable chlorinated rubbers are chlorinated polyethers containing the recurring unit:

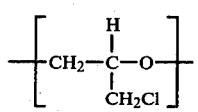

These materials may be homopolymers or copolymers with comonomers, such as ethylene oxide. These copolymers may contain units, such as the ethylene oxide units in random or block distribution.

Because of the interaction occuring between HB polymers and vinyl chloride polymers, particularly interesting materials can be produced by blends thereof. The vinyl chloride polymer is preferably a homopolymer of vinyl chloride or a copolymer containing at least 80% by weight of units derived from vinyl chloride.

As mentioned hereinbefore, the HB polymers act as processing aids. In addition, with larger amounts of HB polymers, the properties depend on whether or not crystallisation of the HB polymer is suppressed. If crystallisation is suppressed so that the composition is essentially amorphous, the HB polymer can act as a toughening agent for vinyl chloride polymers and can be considered as a polymeric plasticiser as well as a processing aid. While other polyesters, e.g. polycaprolactone, are known as polymeric plasticisers for vinyl chloride polymers, they are not satisfactory as processing aids.

At some levels, particularly in the range 10 to 30% by weight of HB polymer, vinyl chloride polymers reduce the rate of crystallisation of the HB polymer thus enabling tough articles to be fabricated. This is of particular utility where the article has a relatively thin section, e.g. less than 2 mm thickness, so that it can be produced by solution casting or by a melt fabrication process where the melt is cooled rapidly as part of the fabrication process to minimise crystallisation. Of course, if such articles are subjected to prolonged periods above the glass transition temperature, Tg, which will vary depending upon the composition and the method by which it is made, crystallisation will occur with consequent loss of the toughening effect. However articles made from such compositions can be used for applications where the temperature is unlikely to exceed Tg. HB copolymers, which are generally less crystalline than the HB homopolymer are particularly useful for toughening vinyl chloride polymers.

At higher HB polymer levels, e.g. above 35% HB polymer, based on the combined weights of the HB polymer and the vinyl chloride polymer, if crystallisation of the HB polymer is induced, e.g. by annealing where necessary, the HB polymer serves to increase the softening temperature of the vinyl chloride polymer enabling vinyl chloride polymer articles to be used at higher service temperatures.

It will be appreciated that the polymer blends may also contain other polymers. For example where a HB polymer is added to a vinyl chloride polymer as a processing aid, or to enhance the heat distortion temperature, an impact modifier such as those normally used for vinyl chloride polymers may also be present: in some cases this impact modifier could be another polymer containing at least 25% by weight of chlorine or nitrile groups, e.g. a chlorinated polyolefin.

When the compositions of the invention contain a substantial amount of chlorine in the form of a chlorine containing polymer, the composition has enhanced fire retardancy relative to the HB polymer itself.

The compositions of the invention may be blended by any of the known techniques for producing an intimate blend of polymers. These techniques include solution blending using a common solvent or melt blending using equipment capable of shearing the melt of polymers. Screw extruders or mills are commonly used for melt blending polymers. It will also be appreciated the blend of polymers may be a simple powder blend providing that the blend is subjected to a homogenising process before or during the process of fabricating an article from the blend. Thus, for example, where an article is formed from the composition in a screw-fed injection-moulding machine, the feed to the hopper of the screw may be a simple mixtue of the two components since an intimate blend may be achieved in the screw portion of the machine.

In addition to the polymeric constituents of the compositions there may also be present any of the auxiliary materials known for use in polymeric compositions such as antioxidants, heat and light stabilisers, plasticisers, pigments reinforcing and non-reinforcing fillers, foaming agents and fire retardants.

Even where the component polymers of the blend are completely miscible (in the thermodynamic sense), as is the case of blends with vinyl chloride polymers, this thermodynamic ideal may not always be realised in practice so that the blends will not be completely mixed but rather have a HB polymer rich phase and a chlorine or nitrile group containing polymer rich phase. The properties of the blends will therefore to some extent depend on the intimacy of mixing of the components.

HB polymers produced by solvent extraction from bacterial cells followed by precipitation are generally in the form of a fine fibrous powder. While this powder may be mixed with the chlorine or nitrile group containing polymer and melt compounded, the fine fibrous HB polymer powder is somewhat difficult to handle and so may be densified, e.g. granulated, before mixing with the chlorine or nitrile group containing polymer. However melt compounding a mixture containing such a densified HB polymer may give inferior dispersion.

We have found that an improved method of obtaining good dispersion of the HB polymer and the chlorine or nitrile group containing polymer is to mix the latter with the precipitated HB powder to which a small amount, e.g. 10% by weight of the blend, of a volatile liquid, e.g. chloroform, has been added. The resultant paste or slurry may then be densified by granulation at a temperature below the melting point of the polymers: before, during, or after granulation the liquid may be removed by volatilisation. This given a densified product that may be readily melt processed.

Even better dispersion may be achieved by mixing the chlorine or nitrile group containing polymer with a solution of the HB polymer in a volatile solvent, e.g. chloroform, followed by such a low temperature granulation process, before, during, or after which the solvent is volatilised. Precipitated HB polymers are generally only poorly soluble in cold solvents and so, where such a solution blending step is required, the precipitation step may be omitted, blending the chlorine or nitrile group containing polymer with the solution obtained by solvent extraction of the HB polymer from the bacterial cells. Alternatively the HB polymer solution may be obtained by heating the precipitated HB polymer with the solvent.

Even more intimate dispersion may, of course, be achieved by mixing solutions of the polymers in a common solvent or in miscible solvents. This is of particular utility where it is desired to fabricate articles by solution casting.

Blends of HB polymers with vinyl chloride polymers may also be made by polymerising the vinyl chloride (and comonomers, if any) in the presence of the HB polymer.

The invention is illustrated by the following examples in which all parts and percentages are expressed by weight, unless the contrary is indicated or implicit. In the examples blends are made from an HB polymer and an additive polymer. In Examples 1 to 15 a complex tin thiooctyl stabiliser based on a di-N-dithioglycollic acid ester (except in Examples 4 and 5a where the stabilizer was a 2,2,4-trimethyl 1,2-dihydroquinoline polymer) was added to the additive polymer, when the latter is used alone, or when blended with the HB polymer, at a level corresponding to 2% of the total composition (except in Examples 1-3 where the amount of stabiliser was 1%).

Various compounding or blending methods are utilised in the Examples as follows:

(a) "Solution" blending.

The precipitated HB polymer is dissolved by refluxing with chloroform followed by cooling to room temperature to give a solution of the HB polymer. The additive polymer and stabiliser is mixed with the solution, the chloroform evaporated off, and the mixture granulated at room temperature in a domestic mincer. The granules are then dried at 60° C. under vacuum for 24 hours, and then melt extruded at 190° C. and regranulated.

(b) "Slurry" blending.

The precipitated HB polymer is dry blended with the additive polymer powder and then about 10% of the blend of chloroform is added to form a paste. The stabiliser is then added and the paste granulated in a domestic mincer at room temperature. The chloroform is removed by volatilisation at 60° C. under vacuum for 24 hours. The granules are then melt extruded at 190° C. and regranulated.

(c) "Melt" blending.

The precipitated HB polymer is made into a paste by addition of 10% of chloroform and granulated and dried as in "slurry" blending. The additive polymer powder, and the stabiliser, are then added to the HB polymer granules and melt compounded, by extrusion followed by granulation unless otherwise indicated.

In the Examples (Except Examples 16b and 16c) the HB polymer was a β-hydroxybutyric acid homopolymer, hereinafter termed PHB, produced by cultivation of *Alcaligenes eutrophus* mutant S 301/C5 (NCIB 11599) on glucose. The PHB was isolated by extraction from the aqueous cell suspension with 1,2-dichloroethane at room temperature followed by separation of the solvent layer, containing the dissolved PHB, from the aqueous layer by decanting. The solution was filtered and then the PHB was precipitated by adding the solution to a methanol/water mixture. The precipitated PHB was separated by filtration and dried. The PHB had a weight average molecular weight (Mw) of about 290,000.

All tensile and impact tests were performed at 23° C. Tensile tests in Examples 1-17, e.g. Tensile Strength (TS), Young's modulus (YM), Elongation to Break (EB) were in accordance with ASTM D638-77a (50 mm/min).

EXAMPLE 1

Blends were made from PHB and various amounts of an amorphous chlorinated polyethylene (CPE) obtained from Dow Chemicals containing 36% chlorine and having a Tg of about −15° C. by "solution" blending. The resultant granules were injection moulded at 190° C. into standard test bars of 3 mm thickness, the properties of which are shown in Table 1.

TABLE 1

| Composition % | | Tensile Properties | | Izod Impact (a) Strength (J/m) | HDT (b) |
|---|---|---|---|---|---|
| PHB | CPE | TS(MNm$^{-1}$) | EB (%) | 1 mm notch | (°C.) |
| 1a | 100 | 0 | 38 | 4 | 27 | 151 |
| 1b | 90 | 10 | 31 | 5 | 32 | 142 |
| 1c | 80 | 20 | 24 | 7 | 37 | 148 |
| 1d | 70 | 30 | 18 | 20 | 59 | 138 |
| 1e | 60 | 40 | 13 | 64 | 96 | 113 |

(a) according to ASTM D256 - 78
(b) Heat Distortion Temperature, according to ASTM D648 using 0.45 N load.

EXAMPLE 2

PHB, and the CPE as used in Example 1, were "melt" blended by extrusion at 190° C. to give granules containing 30% CPE. The granules were injection moulded at 190° C. into standard test pieces of 3 mm thickness using a mould maintained at (a) 25° C. and (b) 65° C. The test pieces were annealed at 50° C. for 48 hours before testing. The results are shown in Table 2.

TABLE 2

| | Mould temp. % | Tensile Properties | | | Izod Impact Strength (J/m) | |
|---|---|---|---|---|---|---|
| | | YM (GNm$^{-2}$) | TS (MNm$^{-2}$) | EB % | 1 mm notch | un-notched |
| 2a | 25 | 2.0 | 16 | 9 | 75 | 350 |
| 2b | 65 | 2.0 | 18 | 15 | 130 | 710 |

EXAMPLE 3

Example 2 was repeated but using as the additive polymer (a) a chlorosulphonated polyethylene (CSPE) of chlorine content (i) 35% and (ii) 43%

(b) an acrylonitride/butadiene/styrene (ABS) polymer which contained less than 25% of nitrile groups.

The mould temperature was 60° C.: the results are shown in Table 3.

TABLE 3

| | Composition (%) | | | Tensile Properties | | | Izod Impact Strength (J/m) | |
|---|---|---|---|---|---|---|---|---|
| | | CSPE | CSPE | | | | | |
| | PHB | 35% Cl | 43% Cl | ABS | YM (GNm$^{-2}$) | TS (MNm$^{-2}$) | EB (%) | 1 mm notch | unnotched |
| 3a | 100 | 0 | 0 | 0 | 3.3 | 40 | 10 | 65 | 115 |
| 3b | 90 | 10 | 0 | 0 | 2.7 | 31 | 19 | 55 | 220 |
| 3c | 70 | 30 | 0 | 0 | 2.2 | 21 | 8 | 120 | 550 |
| 3d | 90 | 0 | 10 | 0 | 3.0 | 31 | 12 | 70 | 420 |
| 3e | 70 | 0 | 30 | 0 | 2.0 | 25 | 50 | 210 | >1000 |
| 3f | 90 | 0 | 0 | 10 | 3.3 | 37 | 4 | 22 | 74 |

This shows that while the CSPE acted as an impact modifier for PHB, the ABS polymer did not.

EXAMPLE 4

Blends of PHB and a chlorinated polyether (CP ether) having a Tg of about −13° C. and containing the repeat unit $$-CH_2-CH-O-$$
$$\quad\quad\quad |$$
$$\quad\quad\quad CH_2Cl$$

were prepared by "melt" blending on a Brabender Plastograph for 3 minutes at a block temperature of 203° C. and a rotor speed of 90 rpm. Samples of the compositions obtained were each formed into plaques of dimensions 10 mm × 10 mm × 1 mm by compression moulding at 180° C. for 2 minutes. The plaques produced were optically clear. The Tg values of the samples and the individual polymeric constituents of the blend were determined using a Du Pont Dynamic Mechanical Analyser using a sample heating rate of 10° C./min. Elongation values were also determined on the plaques. The results are tabulated in Table 4.

TABLE 4

| | Composition (%) | | | |
|---|---|---|---|---|
| | PHB | CP ether | Tg °C. | EB % |
| 4a | 100 | 0 | 27 | 2 |
| 4b | 80 | 20 | 18 | 4 |
| 4c | 70 | 30 | −1 | 366 |
| 4d | 50 | 50 | −3 | 316 |

The DMA showed only a single Tg peak for each sample indicative that the CP ether is miscible with PHB.

EXAMPLE 5

Blends were made from PHB and
(a) the chlorinated polyether used in Example 4
(b) the chlorinated polyethylene used in Example 1
(c) a butyl acrylate rubber,
by "slurry" blending. The resultant granules were injection moulded at 190° C. using a mould temperature of 75° C. into discs of 3 mm thickness and the Impact Strength was measured by the Instrumented Falling Weight Test (IFW). In this test the sample is supported on an annular ring of internal diameter 50 mm and is impacted by dropping an impactor having a weight of 100 N and having a round nose of radius 6 mm. The impactor is dropped from a height such that the velocity at impact is 5 meters/sec. A force transducer is connected to the impactor to give a record of the load on the specimen during the time that it is deformed by the impactor. A permanent record is made of the load-deformation behaviour and the impact strength is calculated from the area under this curve.

The results are shown in Table 5.

TABLE 5

| | Composition (%) | | | | IFW Energy to break (Nm) |
|---|---|---|---|---|---|
| | PHB | CP ether | CPE | butylacrylate rubber | |
| 5a | 100 | 0 | 0 | 0 | 6.5 |
| 5b | 70 | 30 | 0 | 0 | 20.2 |
| 5c | 80 | 0 | 20 | 0 | 11.3 |
| 5d | 70 | 0 | 30 | 0 | 20.1 |
| 5e | 60 | 0 | 40 | 0 | 30.4 |
| 5f | 80 | 0 | 0 | 20 | 2.9 |
| 5g | 70 | 0 | 0 | 30 | 3.6 |
| 5h | 60 | 0 | 0 | 40 | 5.7 |

It is seen from the above examples that the chlorine containing rubbers show a significant toughening effect on PHB. However the butyl acrylate rubber, which is a commonly used impact modifier, shows no toughening effect.

EXAMPLE 6

A series of blends containing 75% PHB were prepared by "melt" blending on a Brabender Plastograph for 2 minutes at a block temperature of 200° C. and a rotor speed of 90 rpm. Samples of the compositions were compression moulded at 200° C. into 1 mm thick test pieces which were then permitted to crystallise isothermally by maintaining the test piece at 60° C. for 5 minutes. The mouldings were examined by optical microscopy and the physical nature assessed manually. The results are set out in Table 6.

TABLE 6

| | Other polymer | Structure | Product nature |
|---|---|---|---|
| 6a | rubbery ethylene/vinyl acetate copolymer containing 28% vinyl acetate | two phase | sticky; brittle |
| 6b | chlorinated polyether (as used in Example 4) | single phase | tough |
| 6c | chlorinated polyethylene (as used in Example 1) | two phase | tough |

Example 6 demonstrates that a conventional impact modifier, viz a rubbery ethylene/vinyl acetate copolymer exhibits no toughening effect whereas the rubbery chlorine containing polymers do act as impact modifiers for PHB.

EXAMPLE 7

Blends of PHB and a vinyl chloride homopolymer (PVC) powder of K-value 67 were made by "slurry" blending. After drying, the granules were melt extruded at 180° C., and regranulated, dried overnight at 60° C. in a vacuum oven, and then injection moulded into test samples of 1.5 mm thickness on an Arburg Allrounder injection moulding machine Model No. 220E—35/90 using a barrel temperature varying from 170° C. at the hopper to 190° C. at the nozzle. A mould temperature of 65° C. and a cooling time of 15-30 seconds was used. The properties of the mouldings are shown in Table 7.

TABLE 7

| Composition (%) | | Tensile Properties | Flexural Modulus | IFW Energy to break | HDT | Vicat[x] (°C.) |
|---|---|---|---|---|---|---|
| PHB | PVC | TS (MNm$^{-2}$) | (GNm$^{-2}$) | (Nm) | (°C.) | 1 kg load |
| 7a | 100 | 0 | 38 | 2.30 | 1.0 | 144 | >150 |
| 7b | 75 | 25 | 36 | 3.0 | 0.4 | 76 | 140 |
| 7c | 50 | 50 | 47 | 3.8 | 0.1 | 68 | 135 |
| 7d | 30 | 70 | 30 | 2.3 | 5.9 | 62.5 | 111 |
| 7e | 25 | 75 | 28 | 2.8 | 24.0 | 56 | 102.5 |
| 7f | 20 | 80 | 27 | 3.1 | 24.0 | 55 | 87.5 |
| 7g | 10 | 90 | 41 | 4.4 | 1.2 | 58.5 | 82 |
| 7h | 0 | 100[xx] | 38 | 3.8 | 3.9 | 71.5 | 86 |

[x]Vicat Softening point according to ASTM D 1525.
[xx]The K 67 PVC was not mouldable under the conditions used to mould the other samples and so a lower viscosity grade PVC, of K-value 57, was used as the control.

Examination of the products containing 20 and 25% PHB showed that they were essentially amorphous, indicating that the vinyl chloride polymer retarded the rate of crystallisation, enabling the PHB to act as a polymeric plasticiser.

The fact that the K-67 PVC was not mouldable under the conditions used, whereas the blends could be moulded, demonstrates that the PHB also acts as a processing aid.

EXAMPLE 8

The procedure of Example 7 was repeated except that the mouldings had a thickness of 3 mm and a mould temperature of 75° C. was employed. The results are shown in Table 8.

TABLE 8

| Composition (%) | | Cooling time | IFW |
|---|---|---|---|
| PVC | PHB | (sec) | Energy to Break (Nm) |
| 8a | 90* | 10 | 30 | 3.2 |
| 8b | 80* | 20 | 40 | 3.1 |
| 8c | 70* | 30 | 40 | 3.3 |
| 8d | 65* | 35 | 35 | 3.1 |
| 8e | 95** | 5 | 15 | 2.3 |
| 8f | 90** | 10 | 20 | 29.4 |
| 8g | 80** | 20 | 25 | 33.4 |
| 8h | 70** | 30 | 30 | 2.3 |
| 8i | 65** | 35 | 30 | 1.8 |

*K-67
**K-57

With the exception of mouldings 8f and 8g, the mouldings were essentially crystalline. This shows that if the cooling rate is too slow, crystallinity can develop, rendering the products brittle.

EXAMPLE 9

Blends of PHB with various polymers were made by "slurry" blending. The granules were examined by differential scanning calorimetry as follows:

The test sample was first heated to 200° C. and held at that temperature for 1.5 minutes and then cooled at a rate of 320° C./min to the desired crystallisation temperature, Tc, and held at that temperature. The time taken at Tc to achieve the maximum rate of crystallisation was measured. The results are shown in Table 9.

TABLE 9

| Composition (%) | | | | Time to maximum crystallisation rate (min) at | | | | | | |
|---|---|---|---|---|---|---|---|---|---|---|
| PHB | PVC | CPE[1] | CP ether[2] | 50° C. | 60° C. | 70° C. | 80° C. | 90° C. | 100° C. | 110° C. |
| 9a | 100 | — | — | — | 1.65 | 0.95 | 0.74 | 0.65 | 0.7 | 0.75 | 4.3 |
| 9b | 60 | — | 40 | — | 3.1 | 2.45 | 1.85 | 2.25 | 2.8 | 4.45 | 11.2 |
| 9c | 60 | — | — | 40 | 6.2 | 4.35 | 4.25 | 5.25 | 9.0 | 22.8 | — |
| 9d | 35 | 65[3] | — | — | — | — | 9.8 | 8.5 | 8.5 | 11.5 | 16.5 |
| 9e | 35 | 65[4] | — | — | — | — | 4.9 | 4.5 | 6.1 | 9.8 | 14.1 |
| 9f | 20 | 80[4] | — | — | too slow to measure | | | | | | |
| 9g | 5 | 94[4] | — | — | too slow to measure | | | | | | |

[1]As used in Example 1
[2]As used in Example 4
[3]K-57
[4]K-67

It is seen that all the additive polymers retarded the rate of crystallisation.

EXAMPLE 10

A weries of blends of PHB and K-57 PVC were made by (a) "solution" blending, (b) "slurry" blending, and (c) "melt" blending by extrusion at 190° C. followed by granulation. The intimacy of mixing is thus expected to be in the order a>b>c.

The resulting granules were moulded into test pieces of thickness 1.6 mm by (i) compression moulding for 2 minutes at 200° C.; the mould and moulding were then quenched in iced water and the mouldings stored at −20° C. until tested to prevent any further crystallisation occuring;

(ii) injection moulding at 190° C. using a mould temperature of 20° C. and a cooling time of 15-30 seconds. The mouldings were stored at −40° C. until tested.

For testing the samples were cooled to −120° C. and Tg determined by dynamic mechanical analysis over the increasing temperature range −120° to 100° C. Further quenched mouldings were annealed at 80° C. in a vacuum oven for 16 hours to develop maximum crystallinity prior to dynamic mechanical analysis. The results are shown in Table 10.

TABLE 10

| | Blend method | Moulding method | An-nealed | Tg (°C.) of blend of PVC/PHB composition | | | |
|---|---|---|---|---|---|---|---|
| | | | | 65/35 | 80/20 | 95/5 | 100/0 |
| 10a | solution | injection | yes | 73.5 | 78 | 78.5 | |
| 10b | slurry | injection | yes | 81 | 85 | 78.5 | |
| 10c | slurry | compression | yes | 89.5 | 86 | 82 | 92.5 |
| 10d | melt | compression | yes | | 94.5 | | |
| 10e | solution | injection | no | 27.5 | 42.5 | 80 | |
| 10f | slurry | injection | no | 36.5 | 55.5 | 75.5 | |
| 10g | slurry | compression | no | 77.5 | 78 | 81.5 | 89.5 |
| 10h | melt | compression | no | | 85 | | |

It is seen that the "solution" blending method gives a lower Tg in the quenched (i.e. unannealed) samples but, on annealing little difference in Tg is obtained. Quenched compression moulded samples do not exhibit such a large depression of Tg. This is probably because the degree of mixing between the two components is not so good as in the case of the injection mouldings.

The Tg of an ideally mixed quenched sample can be predicted from the Fox equation (Bull. Am. Phys. Sec. 1, 1956, page 123)

$$\frac{1}{(Tg) \text{ blend}} = \frac{x}{(Tg) PVC} + \frac{1-x}{(Tg) PHB}$$

where x is the weight fraction of PVC fraction of PVC and the Tg's are in °K. (362.5° K. for PVC and 294° K. for PHB). Comparing the observed Tg's for the quenched "solution" blended samples with values predicted by the Fox equation gives

| Composition (%) | | Tg °C. | |
|---|---|---|---|
| PVC | PHB | predicted | observed |
| 65 | 55 | 62 | 27.5 |
| 80 | 20 | 73 | 42.5 |
| 95 | 5 | 85 | 80 | showing that the Tg depression is greater than predicted by the Fox equation.

EXAMPLE 11

"Solution" and "slurry" blended compositions containing PHB and a K-57 PVC were injection moulded at 190° C. into 1.5 mm thick test pieces using a mould temperature of 20° C. to produce mouldings that were as amorphous as possible. The mouldings were stored at −40° C. until required for testing whereupon they were left at room temperature for 1 hour before impact testing. The 5 kg Vicat softening temperature was also measured. Similar samples were annealed at 75° C. for 16 hours before testing. The results are shown in Table 11.

TABLE 11

| | Composition % | | Blending method | Unannealed | | Annealed | |
|---|---|---|---|---|---|---|---|
| | PVC | PHB | | IFW energy to Break (Nm) | Vicat 5 kg (°C.) | IFW energy to break (Nm) | Vicat 5 kg (°C.) |
| 11a | 95 | 5 | slurry | 9 | 52.5 | 0.5 | 58 |
| 11b | 95 | 5 | solution | 9 | 60 | 0.5 | 65 |
| 11c | 80 | 20 | slurry | 8 | 51 | 0.7 | 76.5 |
| 11d | 80 | 20 | solution | 26.4 | 43 | 0.3 | 70 |
| 11e | 65 | 35 | slurry | 19.3 | 39 | 0.8 | 81.5 |
| 11f | 65 | 35 | solution | 21.7 | 37 | 0.7 | 71 |

The data for the compositions containing 20% PHB show that the intimacy of mixing has a marked effect on the performance of PHB as a toughening agent, i.e. as in the unannealed samples.

EXAMPLE 12

1400 parts of vinyl chloride were polymerised at 61° C. in aqueous suspension in the presence of 120 parts of precipitated PHB powder and 2.55 parts of azodivaleronitrile as initiator, to give 600 parts of a polymer blend containing 20% PHB. A sample of the polymer blend was extracted with cyclohexanone. The soluble portion had a K-value of about 57.

Injection moulded test pieces made as described in Example 10 from the polymer blend were compared with the annealed mouldings of Example 10 made from the "solution" blend of K-57 PVC and PHB containing 20% PHB. The properties are shown in Table 12.

TABLE 12

| Test | Polymerised blend | Solution blend |
|---|---|---|
| IFW Energy to break (Nm) | 1.2 | 0.3 |
| TS (MNm$^{-2}$) | 33.9 | 27.6 |
| EB (%) | 9 | 22 |
| 5 kg Vicat (°C.) | 62 | 70 |
| 1 kg Vicat (°C.) | 120 | — |
| opacity | transparent | translucent |

These properties are indicative that the polymerised blend is more intimately mixed than the solution blend.

EXAMPLE 13

To illustrate the improvements in processability given by the addition of PHB to K-67 PVC, blends were made up by the "solution" and "melt" blending (extrusion at 190° C. techniques and their melt viscosities measured on a melt extruder at 190° C. at a shear stress of $2 \times 10^5$ Nm$^{-2}$. The results are shown in Table 13.

TABLE 13

| | Composition (%) | | Blending method | Viscosity (Nsm$^{-2}$) |
|---|---|---|---|---|
| | PVC | PHB | | |
| 13a | 80 | 20 | solution | $1.4 \times 10^4$ |
| 13b | 80 | 20 | melt | $3.4 \times 10^4$ |
| 13c | 90 | 10 | solution | $5.2 \times 10^4$ |
| 13d | 90 | 10 | melt | $3 \times 10^5$ |
| 13e | 100* | 0 | — | $1 \times 10^6$ |

*K-62 PVC - the K-67 PVC was not melt extrudable at 190° C. in the absence of processing aids.

These results also show that the better mixing technique, "solution" blending, gives a greater viscosity decrease than "melt" blending.

EXAMPLE 14

The procedure of Example 6 was repeated using various chlorine containing polymers:
(i) a chlorinated polyether containing the repeat units

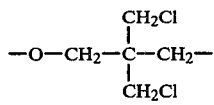

(ii) a chlorinated polyether containing the repeat unit

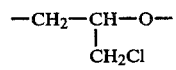

(iii) a chlorinated polybutadiene of Tg about 100° C. and 66% chlorine,
(iv) a chlorinated polyisoprene of Tg about 130° C. and containing 66% chlorine,
(v) a vinylidene chloride/acrylonitrile/methyl methacrylate copolymer containing about 90% vinylidene chloride units, and 3% acrylonitrile units.

In all cases the blends processed readily: in some cases more readily than the additive polymer alone; indeed some of the additive polymers could not be fabricated by themselves satisfactorily at 200° C.

EXAMPLE 15

"Solution" blends were made of K-67 PVC, PHB and chlorinated polyethylene (CPE) as used in Example 1, or a methyl methacrylate/butadiene/styrene rubber (MBS) PVC impact modifier. The resulting granules were injection moulded at 190° C. into test samples of thickness 3 mm using a mould temperature of 60° C. The samples were annealed at 70° C. for 16 hours prior to testing. The results are shown in Table 14.

TABLE 14

| Composition % | | | | Izod Impact Strength (J/m) | | Vicat Softening Point (°C.) | |
|---|---|---|---|---|---|---|---|
| PVC | PHB | CPE | MBS | 1 mm notch | unnotched | 1 kg | 5 kg |
| 15a 100 | 0 | 0 | 0 | 181 | >1000 | 86 | 81 |
| 15b 65 | 35 | 0 | 0 | 36 | 316 | 129 | 78 |
| 15c 60 | 30 | 0 | 10 | 80 | 437 | 122 | 78 |
| 15d 50 | 40 | 10 | 0 | 156 | 286 | 113 | 71 |
| 15e 45 | 35 | 20 | 0 | 56 | 767 | 103 | 68.5 |
| 15f 0 | 70 | 30 | 0 | 130 | >1000 | 151 | 85 |
| 15g 0 | 100 | 0 | 0 | 60 | 200 | 174 | 152 |

EXAMPLE 16

A PVC formulation was made by room temperature dry blending the following ingredients:

| | | parts |
|---|---|---|
| (1) | K-62 vinyl chloride homopolymer | 100 |
| (2) | complex tin thiooctyl stabiliser based on a di-N—dithioglycollic acid ester | 1.5 |
| (3) | methyl methacrylate/butadiene/styrene PVC impact modifier | 8 |
| (4) | wax (external lubricant) | 0.8 |
| (5) | glyceryl monoester (internal lubricant) | 1 |
| (6) | processing aid | 2 |

The processing aids were:
(a) the β-hydroxybutyric acid homopolymer (PHB) as used in the previous examples.
(b) a copolymer (A) containing 75 mole % of β-hydroxybutyric acid units and 25 mole % of β-hydroxyvaleric acid units. This copolymer was prepared in the same manner as the homopolymer except that propionic acid was used as the substrate instead of glucose. The copolymer had a weight average molecular weight (Mw) of about 300,000 and had a melting range, as determined by differential scanning calorimetry of about 120° C. to about 160° C. with a peak in the melting endotherm at 132° C.

(c) a copolymer (B) containing 80 mole % of β-hydroxybutyric acid units and 20 mole % of β-hydroxyvaleric acid units. This copolymer was prepared in the same way as the homopolymer except that, when the aqueous fermentation medium became depleted of a nitrogen source, cultivation was continued using a mixture of glucose and propionic acid as the substrate instead of only glucose. This copolymer had a weight average molecular weight (Mw) of about 300,000 and a melting range of about 100° C. to about 180° C., with a peak in the melting endotherm at 168° C.

(d) polycaprolactone of melting point 60° C.

The processing aids were melt extruded and ground to a particle size below 150 μm before incorporation into the PVC dry blend.

The dry blends were tested as follows:

(1) 50 g of the mixture was poured into the mixing head of a Brabender Plastograph maintained at 180° C. rotating at 18 rpm under a pressure ram loaded with a 5 kg weight. The time taken for gelation to occur was measured.

(2) The mixture was cold compressed to form a candle which was then charged to an extrusion rheometer maintained at 170° C. and fitted with a die having a circular orifice of 1 mm diameter and 20 mm land length. After the charge had heated to 170° C., it was extruded at increasing rates. The appearance of the extrudate was noted and the melt extensibility assessed by attempting to draw the extrudate away from the die. The results are shown in Table 15.

TABLE 15

| Processing aid | Gelation time (min) at 180° C. | Extrusion at 170° C. | |
|---|---|---|---|
| | | Appearance | Melt extensibility |
| 16a none | 12 | Severe sharkskin at low extrusion rates; ripple at higher rates | Poor |
| 16b homopolymer | 9.5 | poor with a lot of unmelted polymer clearly visible | Poor |
| 16c copolymer A | 1.0 | excellent - very smooth | good |
| 16d copolymer B | 1.5 | smooth but occasional unmelted particles | fair |
| 16e polycaprolactone | 1.5 | fair at low extrusion rates; severe ripple at higher rates | fair |

The results for the homopolymer and copolymer B are indicative that the processing temperature of 170° C. was too low for complete melting of the processing aid to occur. Likewise, for the homopolymer, the long gelation time at 180° C. is indicative that 180° C. is too low a processing temperature.

EXAMPLE 17

In this Example PHB was assessed as a processing aid for a high acrylonitrile resin obtained by the graft polymerisation of about 75 parts of acrylonitrile and 25 parts of methyl acrylate in the presence of about 9 parts of a butadiene/acrylonitrile rubber containing 70% butadiene. This high acrylonitrile resin thus contains about 35% nitrile groups.

Blends were made from 100 parts of the acrylonitrile resin and 2 parts of β-hydroxybutyric acid homopolymer (PHB), as used in the previous examples, by mixing the acrylonitrile resin with PHB powder obtained by melt extruding PHB followed by grinding to a particle size below 150 μm.

The resulting blend was (i) extruded at 200° C., and (ii) injection moulded into standard test bars of thickness 3 mm at 200° C. using a mould temperature of 60° C. For comparative purpose the extrusion and injection moulding were repeated with the acrylonitrile resin alone, i.e. with no processing aid.

Addition of the processing aid significantly reduced the power required for extrusion and increased the extrusion rate. In injection moulding, the screw back time and injection pressure were significantly reduced by addition of the PHB.

The mouldings were tested (a) as made and (b) after annealing for 24 hours at 50° C.

The results are shown in Table 16.

TABLE 16

| | Composition (parts) | | | Tensile properties | | | Izod Impact Strength (J/m) | |
|---|---|---|---|---|---|---|---|---|
| | nitrile resin | PHB | Annealed | YM (GNm$^{-2}$) | TS (MNm$^{-2}$) | EB (%) | 1 mm notch | Unnotched |
| 17a | 100 | 0 | no | 3.63 | 57 | 10–20 | 110–150 | 350–650 |
| 17b | 100 | 2 | no | 4.18 | 68 | 26–33 | 370–500 | 1000 |
| 17c | 100 | 0 | yes | 3.50 | 65 | 8–10 | 90–130 | 300–400 |
| 17d | 100 | 2 | yes | 3.86 | 70 | 20–23 | 250–320 | 1000 |

The above results indicate that not only does the PHB assist processing but also improves the mechanical properties.

EXAMPLE 18

Tubular film of thickness 0.12 mm was made from the acrylonitrile resin blends made as described in Example 17 containing varying amounts of PHB as a processing aid by melt extrusion at 200° C. through an annular die. As in Example 17, incorporation of the PHB reduced the power required for extrusion and increased the extrusion rate.

The tensile strength and Young's modules (measured according to ASTM D882-79); and tensile impact strength (measured according to ASTM D1822-68) were determined. Measurements were made in both the machine and transverse directions and as the direction of testing gave little difference in the results, the measurements were averaged. The permeability to oxygen was measured according to ASTM D1434-75.

TABLE 17

| Composition (parts) | | Tensile properties | | | Permeability |
|---|---|---|---|---|---|
| acrylonitrile resin | PHB | TS (MNm$^{-2}$) | YM (GNm$^{-2}$) | Impact strength (kJm$^{-2}$) | ml · m$^{-2}$ · day$^{-1}$ · atm$^{-1}$ |
| 100 | 0 | 52 | 3.04 | 181 | 3.2 |
| 99.5 | 0.5 | 51 | 2.90 | 168 | 3.2 |
| 99 | 1 | 49 | 2.80 | 186 | 2.9 |
| 98 | 2 | 52 | 3.12 | 184 | 3.1 |

These results show that while the addition of PHB improved processability, it had no adverse effect on the film properties.

We claim:

1. A polymer blend comprising (i) 0.2 to 95% by weight of a β-hydroxybutyric acid polymer of molecular weight above 50,000 and containing 100 to 50 mole % of β-hydroxybutyric acid residues and correspondingly 0–50 mole % of β-hydroxyvaleric acid residues in the polymer chain, and (ii) an organic polymer containing at least 25% by weight of chlorine and/or nitrile groups.

2. A polymer blend according to claim 1 wherein said organic polymer is a polymer containing at least 50% by weight of units derived from vinyl chloride, vinylidene chloride, and/or acrylonitrile and 0 to 50% by weight of units derived from at least one other ethylenically unsaturated monomer.

3. A polymer blend according to claim 2 wherein said organic polymer is a graft copolymer of (i) 99.5 to 50% by weight of a monomer mixture containing at least 50% by weight of acrylonitrile and 0 to 50% by weight of at least one comonomer on (ii) 0.5 to 50% by weight of a butadiene/acrylonitrile copolymer trunk.

4. A polymer blend according to claim 1 wherein said organic polymer is a chlorinated, or chlorosulphonated, hydrocarbon polymer.

5. A polymer blend according to claim 4 wherein said organic polymer is a chlorinated or chlorosulphonated polyolefin.

6. A polymer blend according to claim 5 wherein said organic polymer is a chlorinated or chlorosulphonated polyethylene.

7. A polymer blend according to claim 1 wherein said organic polymer is a chlorinated polyether.

8. A polymer blend according to any one of claims 4 to 7 wherein said organic polymer has a glass transition temperature below 10° C.

9. A polymer blend according to claim 8 containing 10 to 50% by weight of said organic polymer.

10. A polymer blend according to claim 2 containing less than 50% by weight of the β-hydroxybutyric acid polymer.

11. A polymer blend according to claim 10 wherein the β-hydroxybutyric acid polymer is a copolymer containing 1 to 40 mole % of comonomer units.

12. A polymer blend according to claim 2 wherein said organic polymer is a polymer of vinyl chloride containing at least 80% by weight of units derived from vinyl chloride.

13. A polymer blend according to claim 12 containing 10 to 30% by weight of the β-hydroxybutyric acid polymer.

14. A polymer blend according to claim 1 wherein the β-hydroxybutyric acid polymer has a molecular weight above 100,000.

15. A polymer blend according to claim 13 in the form of a shaped article having a thickness of less than 2 mm.

16. A method of making a polymer blend according to claim 1 comprising blending the organic polymer with a solution of the β-hydroxybutyric acid polymer in a volatile solvent and then removing said solvent by volatilisation.

17. A method of making a polymer blend according to claim 1 comprising forming a slurry of the organic polymer, the β-hydroxybutyric acid polymer and a volatile liquid and then removing said liquid by volatilisation.

18. A method according to claim 16 or claim 17 wherein the mixture is granulated before, during, or after, volatilisation of the liquid.

19. A method of making a polymer blend according to claim 12 comprising polymerising a monomeric material containing at least 80% by weight of vinyl chloride in the presence of the β-hydroxybutyric acid polymer.

20. A method of making shaped articles comprising fabricating a polymer blend according to claim 1 at a temperature above the melting point of the β-hydroxybutyric acid polymer but below 220° C.

* * * * *